(12) United States Patent
Kuroda et al.

(10) Patent No.: US 11,317,925 B2
(45) Date of Patent: May 3, 2022

(54) OSTEOTOMY SURGICAL APPARATUS

(71) Applicant: OLYMPUS TERUMO BIOMATERIALS CORP., Tokyo (JP)

(72) Inventors: Koichi Kuroda, Kanagawa (JP); Mitsuya Urata, Kanagawa (JP); Ryohei Takeuchi, Kanagawa (JP)

(73) Assignee: OLYMPUS TERUMO BIOMATERIALS CORP., Tokyo (JP)

( * ) Notice: Subject to any disclaimer, the term of this patent is extended or adjusted under 35 U.S.C. 154(b) by 238 days.

(21) Appl. No.: 16/256,285

(22) Filed: Jan. 24, 2019

(65) Prior Publication Data

US 2019/0150945 A1 May 23, 2019

Related U.S. Application Data

(63) Continuation of application No. PCT/JP2016/071887, filed on Jul. 26, 2016.

(51) Int. Cl.
*A61B 17/16* (2006.01)
*A61B 17/15* (2006.01)
*A61B 90/00* (2016.01)
*A61B 17/80* (2006.01)

(52) U.S. Cl.
CPC .......... *A61B 17/154* (2013.01); *A61B 17/152* (2013.01); *A61B 17/16* (2013.01); *A61B 17/1675* (2013.01); *A61B 17/8095* (2013.01); *A61B 90/06* (2016.02); *A61B 2090/0801* (2016.02)

(58) Field of Classification Search
CPC ..... A61B 17/14; A61B 17/151–17/158; A61B 17/16–17/1697
See application file for complete search history.

(56) References Cited

U.S. PATENT DOCUMENTS

| 1,584,021 | A | * | 5/1926 | Dunn | B25B 27/00 |
| | | | | | 30/172 |
| 2,455,655 | A | * | 12/1948 | Carroll | A61B 17/142 |
| | | | | | 606/178 |
| 5,047,043 | A | * | 9/1991 | Kubota | A61B 17/320016 |
| | | | | | 606/169 |
| 5,058,274 | A | * | 10/1991 | Smith | B44D 3/164 |
| | | | | | 30/169 |
| 5,391,169 | A | | 2/1995 | McGuire | |
| 5,725,530 | A | * | 3/1998 | Popken | A61B 17/15 |
| | | | | | 30/166.3 |
| 6,233,832 | B1 | * | 5/2001 | Berns | B26B 5/00 |
| | | | | | 30/162 |

(Continued)

FOREIGN PATENT DOCUMENTS

| CN | 201244060 Y | 5/2009 |
| CN | 102335021 A | 2/2012 |

(Continued)

OTHER PUBLICATIONS

Extended Supplementary European Search Report dated Jan. 3, 2020 in European Patent Application No. 16 91 0484.1.

(Continued)

*Primary Examiner* — Zade Coley
(74) *Attorney, Agent, or Firm* — Scully, Scott, Murphy & Presser, P.C.

(57) ABSTRACT

An osteotomy surgical apparatus according to the present invention includes a bone cutting blade used for cutting bone tissue and a guard disposed so as to overlap the bone cutting blade in a side view of the bone cutting blade. A distal end of the guard is disposed at a position retracted rearward relative to a blade edge of the bone cutting blade.

5 Claims, 15 Drawing Sheets

(56) References Cited

U.S. PATENT DOCUMENTS

| | | | |
|---|---|---|---|
| 8,287,597 B1 | 10/2012 | Pimenta et al. | |
| 8,938,883 B2* | 1/2015 | Gringer | B26B 1/046 30/155 |
| 2005/0193568 A1* | 9/2005 | Peyrot | B26B 29/02 30/162 |
| 2005/0273112 A1 | 12/2005 | McNamara | |
| 2007/0083209 A1 | 4/2007 | Schenberger et al. | |
| 2007/0118145 A1* | 5/2007 | Fischer | A61B 17/1671 606/99 |
| 2008/0243125 A1* | 10/2008 | Guzman | A61B 17/142 606/82 |
| 2011/0034945 A1 | 2/2011 | Paulos | |
| 2011/0213370 A1 | 9/2011 | Nakamura | |
| 2014/0100577 A1 | 4/2014 | Guzman et al. | |
| 2019/0090887 A1 | 3/2019 | Paulos | |

FOREIGN PATENT DOCUMENTS

| | | |
|---|---|---|
| EP | 1974679 A2 | 10/2008 |
| JP | S62-213747 A | 9/1987 |
| JP | 2007-536011 A | 12/2007 |
| JP | 2008-284342 A | 11/2008 |
| JP | 2010-110597 A | 5/2010 |
| JP | 2015-016095 A | 1/2015 |
| KR | 2013-0113137 A | 10/2013 |
| WO | WO 1999/020184 A1 | 4/1999 |
| WO | 2005/117724 A2 | 12/2005 |
| WO | WO 2006/022923 A1 | 3/2006 |
| WO | 2007/041027 A2 | 4/2007 |
| WO | 2009/129272 A2 | 10/2009 |

OTHER PUBLICATIONS

Chinese Office Action dated Jun. 16, 2021 received in 201680087931.7.

International Search Report dated Sep. 13, 2016 issued in PCT/JP2016/071887.

Japanese Notification of Reasons for Refusal dated May 16, 2017 issued in JP 2013-144777.

* cited by examiner

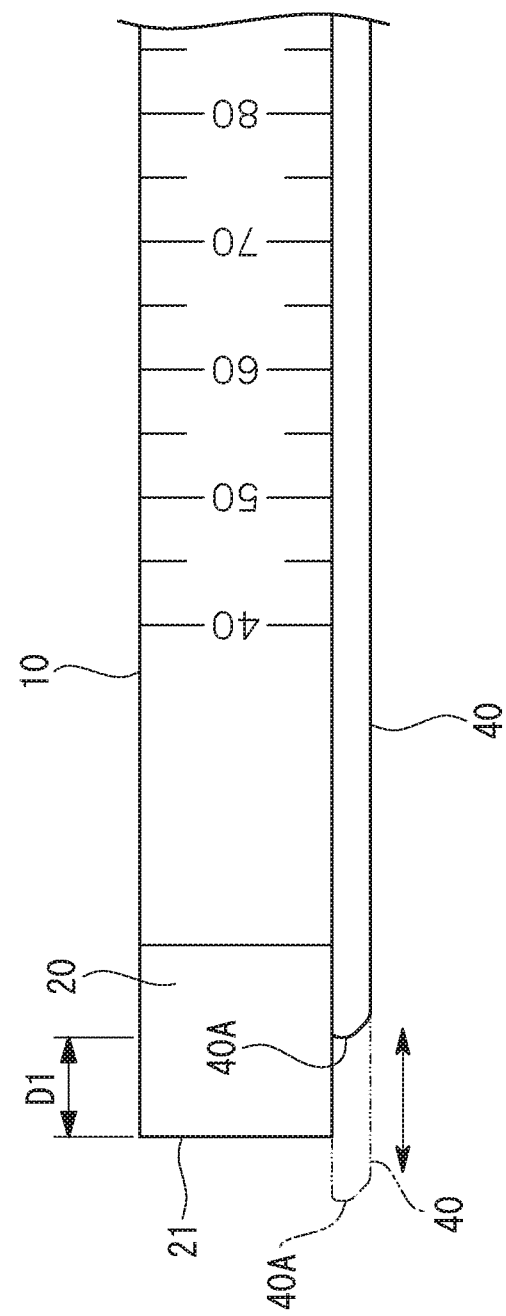

OSTEOTOMY SURGICAL APPARATUS

CROSS-REFERENCE TO RELATED APPLICATIONS

This is a continuation of International Application PCT/JP2016/071887, with an international filing date of Jul. 26, 2016, which is hereby incorporated by reference herein in its entirety.

TECHNICAL FIELD

The present invention relates to osteotomy surgical apparatuses, and particularly, to an osteotomy surgical apparatus used for, for example, knee osteoarthritis.

BACKGROUND ART

In the related art, a high tibial osteotomy (HTO) has been performed for knee osteoarthritis (knee OA). This surgery involves correcting and adjusting the alignment of a proximal shin bone having varus deformity and shifting a large portion of the load acting lopsidedly on the medial joint of the knee toward the lateral joint.

An HTO can be largely classified into two kinds, which are a lateral closed wedge HTO (CWHTO) involving cutting off a laterally open wedge-like bone fragment from a shin bone and a medial open wedge HTO (OWHTO) involving opening an incision made at the medial side of a shin bone by using, for example, a chisel. In either operative procedure, an osteotomy surgical apparatus is used to make an incision in the horizontal direction relative to the shin bone.

Japanese Unexamined Patent Application, Publication No. 2015-16095 discloses an example of an osteotomy surgical apparatus. This osteotomy surgical apparatus is also called a bone chisel and is provided with a bone cutting blade at one end thereof and a striking section, at the other end, to be struck with a hammer. By setting the blade edge of the bone cutting blade on a bone and striking the striking section with, for example, a hammer, the bone can be cut using the bone cutting blade.

Because the dorsal side of a knee has soft tissue, such as nerves and blood vessels, it is necessary to accurately cut the rigid bone while protecting the soft tissue. The osteotomy surgical apparatus proposed in Japanese Unexamined Patent Application, Publication No. 2015-16095 is provided with a guard at a side surface of the bone cutting blade so as to cover the side surface including the blade edge. With such an apparatus, an osteotomy can be performed while using the guard inserted between the bone and the soft tissue to protect the soft tissue surrounding the bone cutting blade.

SUMMARY OF INVENTION

A first aspect of the present invention provides an osteotomy surgical apparatus including: a bone cutting blade used for cutting bone tissue; and a guard disposed so as to overlap the bone cutting blade in a side view of the bone cutting blade, wherein a distal end of the guard is disposed at a position retracted rearward relative to a blade edge of the bone cutting blade.

A second aspect of the present invention provides an osteotomy surgical apparatus including: a bone cutting blade used for cutting bone tissue; and a guard, wherein the guard is biased by a biasing means at least toward a position where the guard overlaps a blade edge of the bone cutting blade, and is slidable rearward in accordance with a force received from the bone tissue.

BRIEF DESCRIPTION OF DRAWINGS

FIG. 6 is a plan view illustrating the distal end of an osteotomy surgical apparatus according to a second embodiment of the present invention.

DESCRIPTION OF EMBODIMENTS

First Embodiment

A first embodiment of the present invention will be described with reference to FIGS. 1 to 5.

Figure 1:
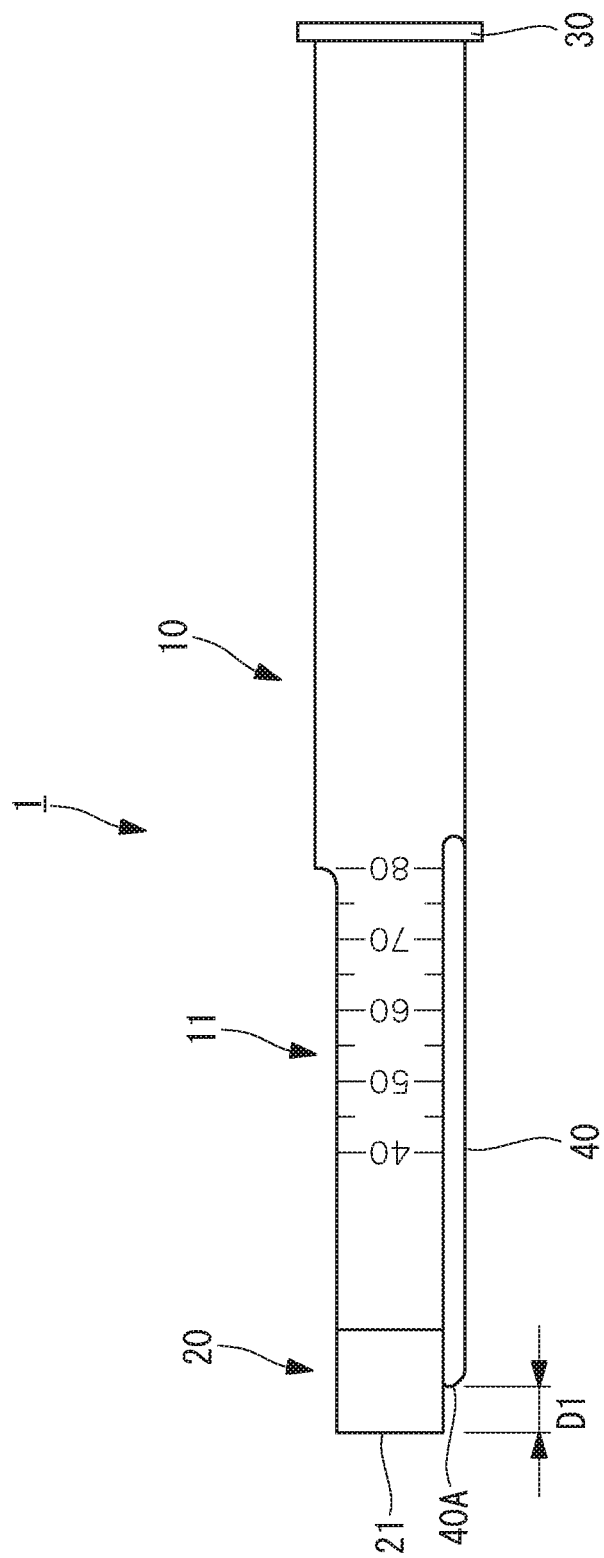
FIG. 1 is a plan view illustrating the overall configuration of an osteotomy surgical apparatus according to a first embodiment of the present invention.

FIG. 1 is a plan view illustrating the overall configuration of an osteotomy surgical apparatus (simply referred to as "surgical apparatus" hereinafter) 1 according to this embodiment. The surgical apparatus 1 includes a plate-like main body 10, a bone cutting blade 20 provided at a first end of the main body 10 and used for cutting bone tissue, a striking section 30 provided at a second end of the main body 10, and a guard 40 attached to the bone cutting blade 20.

The main body 10 is composed of a biocompatible metal, such as stainless steel or titanium, and has a plate-like shape extending in the longitudinal direction. Although the main body 10 is not particularly limited in shape, since the bone cutting blade 20 side of the main body 10 is to be inserted into tissue by a certain length during a procedure, it is preferable that the main body 10 be relatively thin, like a plate, to reduce resistance during the insertion process.

With regard to the main body and the bone cutting blade in the present invention, a pair of relatively large side surfaces at opposite sides in the thickness direction are defined as an upper surface and a lower surface, respectively, and a pair of relatively small surfaces located between the upper surface and the lower surface are defined as side surfaces.

The bone cutting blade 20 decreases in thickness gradually with increasing distance from the main body 10, such that the farthest end from the main body 10 serves as a blade edge 21 having the smallest thickness. The blade edge 21 is not limited in terms of its forming method. The bone cutting blade 20 may be a so-called single-edged blade having an inclined surface only on one side in the thickness direction or a so-called double-edged blade having inclined surfaces on both sides in the thickness direction. In this embodiment, the main body 10 and the bone cutting blade 20 are formed as a single piece by using the same material.

The outer surface of the main body 10 is provided with a scale 11 indicating the distance from the blade edge 21. Accordingly, the position of the blade edge 21 can be roughly ascertained from the scale 11 even if the blade edge 21 is inserted in tissue and is thus not visible.

The striking section 30 is attached to the main body 10 such that the thickness direction of the striking section 30 is parallel (including substantially parallel) to the longitudinal direction of the main body 10, and opposite surfaces of the striking section 30 in the thickness direction are substantially square-shaped. The striking section 30 is not particularly limited to this shape so long as the area thereof in the thickness direction is of an appropriate size for striking the striking section 30 with, for example, a hammer. For example, the opposite surfaces in the thickness direction may be circular or elliptical. Moreover, the thickness or the diameter of the base end of the main body 10 at the opposite side from the bone cutting blade 20 may be increased so that the striking section 30 is integrated with the main body 10.

Furthermore, the material of the striking section 30 is not particularly limited so long as it has enough rigidity against an impact from, for example, a hammer, and may either be the same as or different from the material of the main body 10.

Figure 2:
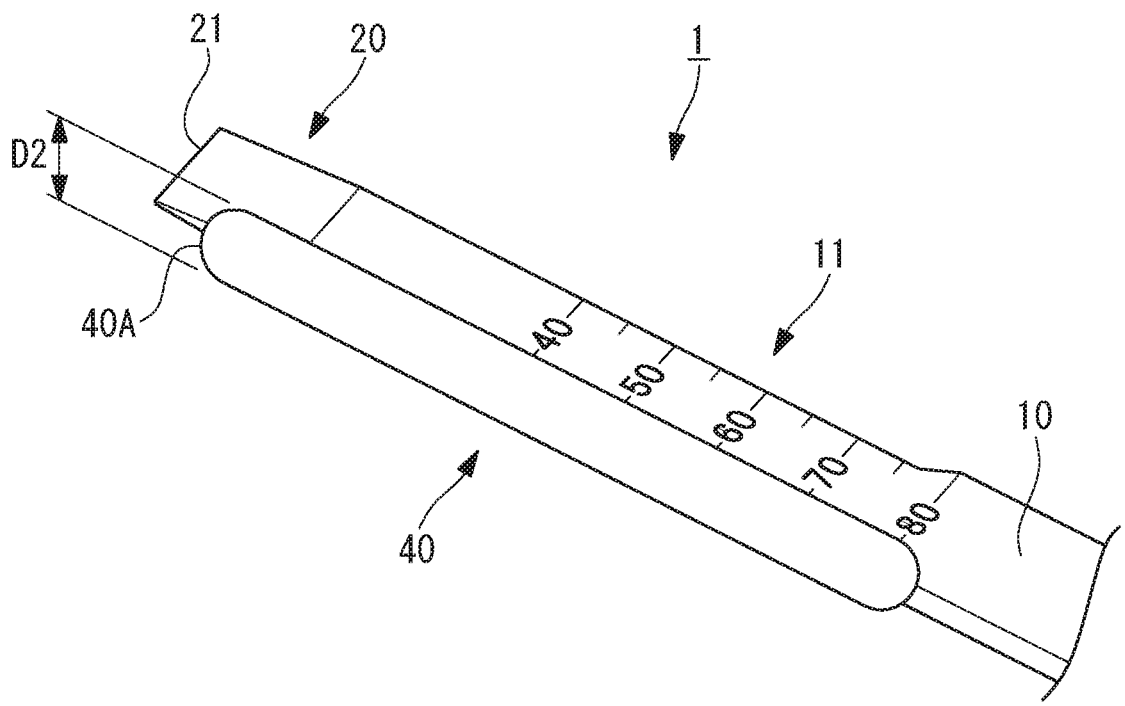
FIG. 2 is an enlarged perspective view illustrating the distal end of the surgical apparatus.

FIG. 2 is an enlarged perspective view illustrating the distal end of the surgical apparatus 1. The guard 40 according to this embodiment is composed of the same material as the main body 10. As shown in FIGS. 1 and 2, the guard 40 is attached toward the base end relative to the blade edge 21 and covers the left side surface of the bone cutting blade 20. A distal end 40A of the guard 40 recedes toward the rear (i.e., toward the base end) relative to the blade edge 21. The guard 40 basically has an elliptical plate-like shape and is attached to the bone cutting blade 20 such that the surface direction of the main body 10 and the surface direction of the guard 40 are orthogonal (including substantially orthogonal) to each other.

A distance D1 between the distal end 40A of the guard 40 and the blade edge 21 in a direction parallel to the longitudinal direction of the main body 10 is preferably larger than 0 mm and smaller than or equal to 10 mm, and more preferably ranges between 3 mm and 6 mm inclusive. If the distance D1 exceeds 10 mm, it becomes difficult for the guard 40 to protect soft tissue around the blade edge 21.

The guard 40 has a width D2 that is larger than the thicknesses of the main body 10 and the bone cutting blade 20, such that the guard 40 protrudes from opposite sides of the bone cutting blade 20 in the thickness direction. The guard 40 has a plate-like shape but has rounded corners and edges so as not to apply excessive pressure to tissue in contact therewith.

The operation when the surgical apparatus 1 having the above-described configuration is in use will now be described with reference to an example of a procedure where an incision is made in a shin bone at the dorsal side thereof in an HTO.

Figure 3:
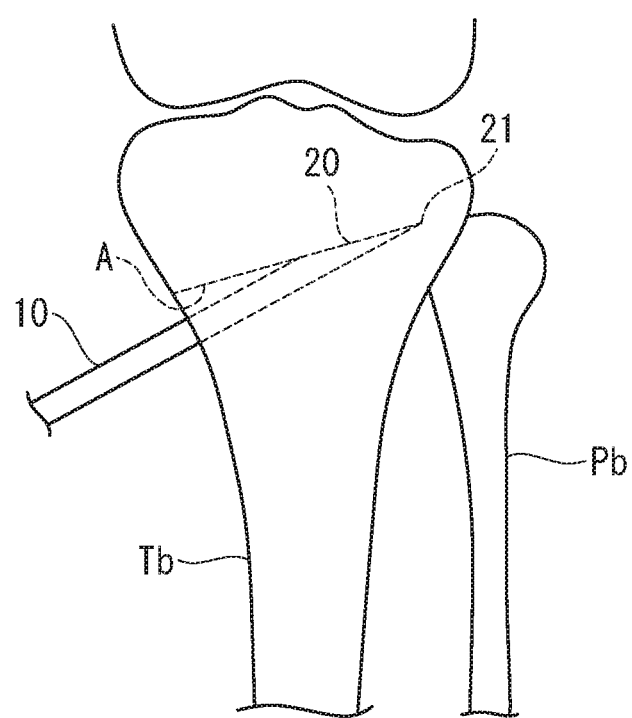
FIG. 3 schematically illustrates the surgical apparatus driven into a shin bone, as viewed from the ventral side.
Figure 4:
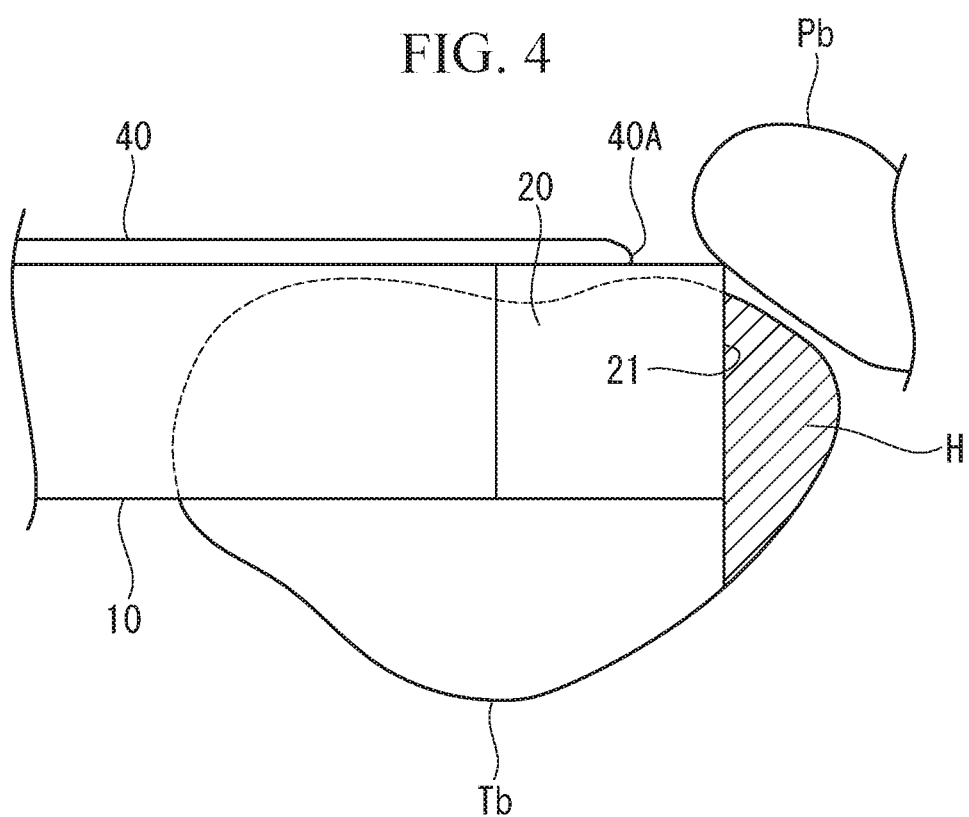
FIG. 4 schematically illustrates the surgical apparatus driven into the shin bone, as viewed from the head.

A surgeon incises skin and tissue at the inner side of a proximal shin bone and inserts the distal end of the surgical apparatus 1 to bring the blade edge 21 into contact with the shin bone. In this case, the guard 40 is disposed between the shin bone and soft tissue, such as muscles and blood vessels. In this state, when the striking section 30 is struck with, for example, a hammer, the bone cutting blade 20 is driven into the shin bone, so that an incision A is made in a shin bone Tb, as shown in FIG. 3. The incision A extends to an intermediate position of the shin bone Tb, so that a hinge H serving as a fulcrum when opening the incision A is made in an outer section of the shin bone Tb, as shown in FIG. 4. FIG. 3 illustrates the shin bone Tb and a calf bone Pb, as viewed from the ventral side, and FIG. 4 is a cross-sectional view of the shin bone Tb and the calf bone Pb, taken along the incision A.

Figure 5:
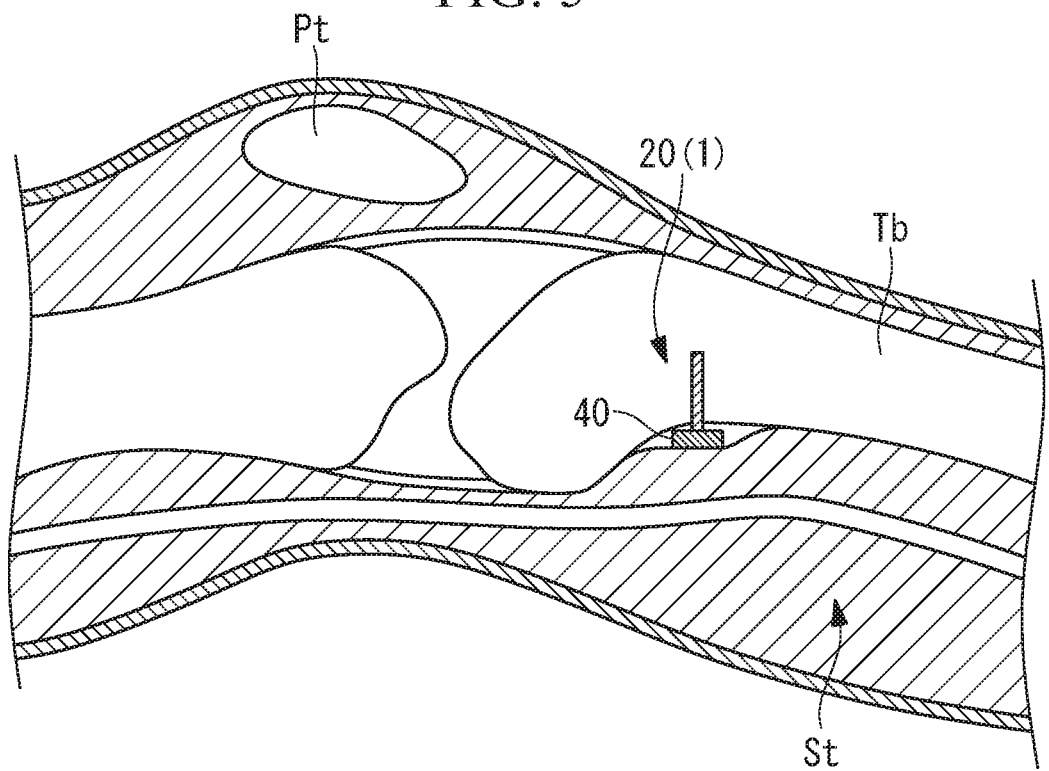
FIG. 5 schematically illustrates the positional relationship among tissues near a knee joint.

FIG. 5 schematically illustrates the positional relationship among tissues near a knee joint. In FIG. 5, the calf bone has been omitted. In FIG. 5, the upper side with a knee cap Pt is the ventral side, whereas the lower side opposite therefrom is the dorsal side. As shown in FIG. 5, soft tissue St exists at the dorsal side of the shin bone Tb. When the blade edge 21 deviates toward the dorsal side due to an impact from, for example, a hammer, there is a possibility of damaging the soft tissue St.

Since the guard 40 is attached to the bone cutting blade 20, when the surgical apparatus 1 according to this embodiment is driven into the shin bone Tb such that the guard 40 is inserted between the shin bone Tb and the soft tissue St, the soft tissue St around the bone cutting blade 20 is more favorably protected by the guard 40, as shown in FIG. 5. Even if the blade edge 21 faces the soft tissue St due to an impact from, for example, a hammer, the guard 40 presses the soft tissue St away from the shin bone Tb, so that the blade edge 21 is less likely to come into contact with the soft tissue St.

As described above, the surgical apparatus 1 according to this embodiment includes the guard 40 so that the osteotomy on the dorsal side of a shin bone, which requires utmost attention, can be appropriately performed while minimizing effects on soft tissue surrounding the bone.

Furthermore, because the blade edge 21 protrudes forward more than the distal end 40A of the guard 40, the distal end 40A of the guard 40 is prevented from abutting on the calf bone Pb, which is located at the outer dorsal side of the shin bone Tb, before the blade edge 21 abuts on the calf bone Pb in the process of driving the bone cutting blade 20. The calf bone Pb has protrusions and recesses, and the position and shape of the calf bone Pb vary from individual to individual. By causing the blade edge 21 to reach a desired depth of the shin bone Tb regardless of the shape of the calf bone Pb, the incision A can be reliably made to the desired depth.

In order to protect soft tissue in an HTO in the related art, the osteotomy is performed while separating the soft tissue from a shin bone by using, for example, a metallic retractor. In contrast, the surgical apparatus 1 includes the guard 40 that functions also as a retractor, so that the osteotomy can be performed alone, unlike the procedure in the related art where a surgical apparatus and a retractor are normally manipulated by different people.

Second Embodiment

A second embodiment of the present invention will now be described with reference to FIGS. 6 to 7D. This embodiment differs from the first embodiment in terms of the configuration of the guard. In the following description, components that are the same as those described above are given the same reference signs, and redundant descriptions are omitted.

FIG. 6 is a plan view illustrating the distal end of a surgical apparatus according to this embodiment. As shown in FIG. 6, the guard 40 according to this embodiment is attached to the bone cutting blade 20 via the main body 10 in a slidable manner between a first position (see the two-dot chain line) and a second position (see the solid line) in the direction parallel to the longitudinal direction of the main body 10. The first position is a position where the distal end 40A protrudes forward more than the blade edge 21 and where the guard 40 covers the left side surface of the bone cutting blade 20 including the blade edge 21. The second position is a position where the distal end 40A is retracted rearward relative to the blade edge 21. The distance D1 at the second position is preferably designed within the same range as the distance D1 in the first embodiment.

The guard 40 is biased toward the first position by a biasing means. When a force acting toward the base end is applied to the guard 40, the guard 40 slides toward the second position against the biasing force of the biasing means.

Figure 7A:
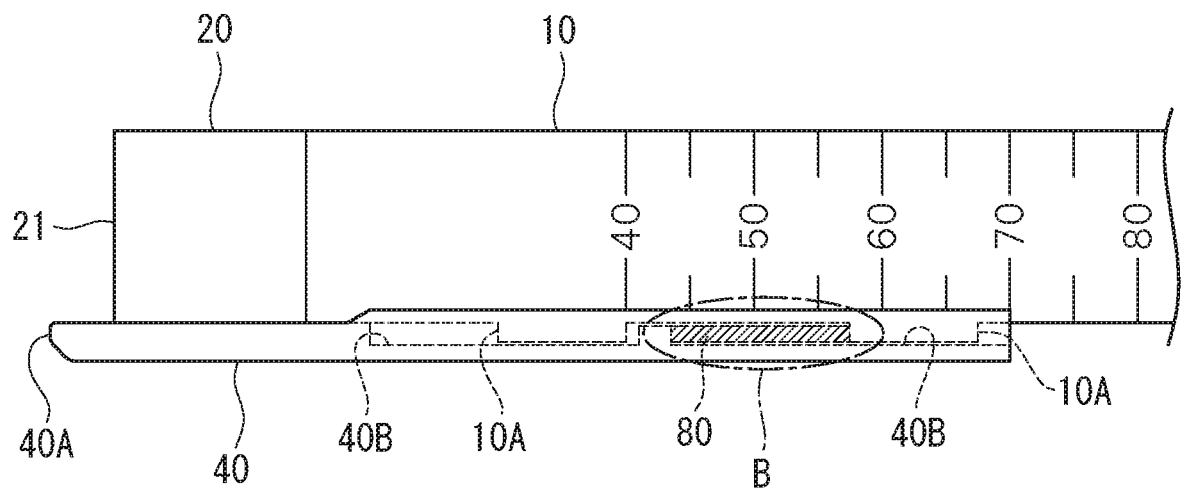
FIG. 7A illustrates an example of a structure for attaching a guard to a bone cutting blade in the surgical apparatus.
Figure 7B:
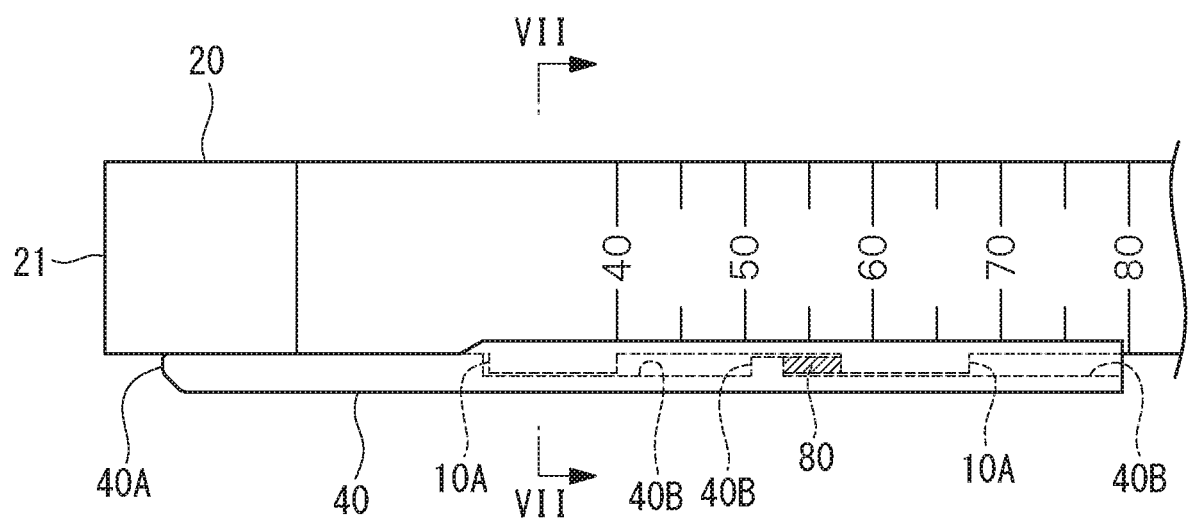
FIG. 7B illustrates the example of the structure for attaching the guard to the bone cutting blade in the surgical apparatus.
Figure 7C:
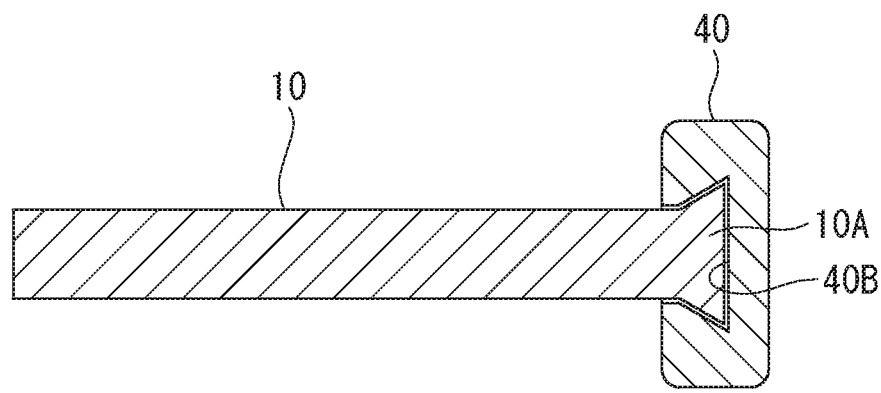
FIG. 7C is a cross-sectional view taken along line VII-VII in FIG. 7B.
Figure 7D:
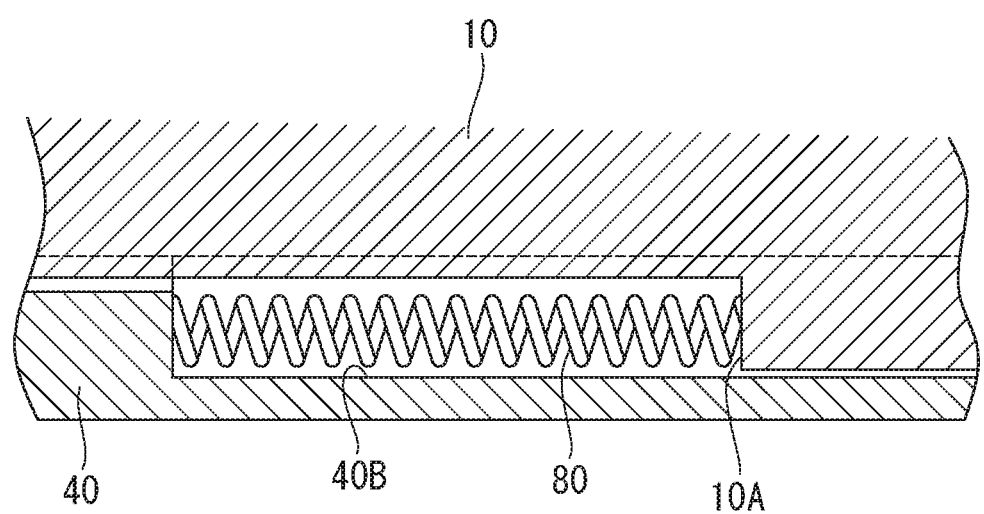
FIG. 7D is an enlarged vertical-sectional view of a region B in FIG. 7A.

FIGS. 7A to 7D illustrate an example of the biasing means and the structure for attaching the guard 40 to the main body 10. As shown in FIGS. 7A and 7B, the left side surface of the main body 10 is provided with a protrusion 10A protruding laterally from the main body 10, and, at a position where the guard 40 faces the protrusion 10A, the guard 40 is provided with a groove 40B that extends in the longitudinal direction and to which the protrusion 10A is fitted. As shown in FIG. 7C, the protrusion 10A has a shape of a dovetail tenon, and the groove 40B has a shape of a dovetail groove. Accordingly, the guard 40 is joined to the main body 10 in a movable manner in the longitudinal direction of the main body 10.

The protrusion 10A and the groove 40B are at least provided at two locations spaced apart from each other in the direction parallel to the longitudinal direction of the main body 10, so that the guard 40 is positionally stable relative to the main body 10. As shown in FIG. 7D, a biasing means 80 includes an elastic member, such as a coil spring, contractible in the direction parallel to the main body 10. The biasing means 80 is provided between a distal-end outer surface of the protrusion 10A and a distal-end inner surface of the groove 40B, which face each other. When the biasing means 80 contracts, the guard 40 moves from the first position shown in FIG. 7A toward the second position shown in FIG. 7B.

Next, the operation when the surgical apparatus according to this embodiment is in use will be described.

A surgeon incises skin and tissue at the inner side of a proximal shin bone and inserts the distal end of the surgical apparatus to bring the blade edge 21 into contact with the shin bone. In this case, the distal end 40A of the guard 40 is inserted between the shin bone and soft tissue, such as muscles and blood vessels. In this state, when the striking section 30 is struck with, for example, a hammer, the bone cutting blade 20 is driven into the shin bone, so that an incision is made in the shin bone.

When the distal end 40A of the guard 40 protruding from the blade edge 21 abuts on the calf bone in the process of driving the bone cutting blade 20, the guard 40 receives a force acting toward the base end from the calf bone and slides toward the base end. Thus, a problem in which the guard 40 is stopped by the calf bone and the blade edge 21 thus cannot be inserted to a position where it touches the shin bone is prevented. Consequently, the blade edge 21 is caused to reach a desired depth of the shin bone, so that an incision can be reliably made to the desired depth.

Since other advantages of this embodiment are the same as those in the first embodiment, descriptions thereof are omitted.

Third Embodiment

A third embodiment of the present invention will now be described with reference to FIGS. 8 to 16. This embodiment differs from the first embodiment in terms of the shape of the main body and the configuration of the guard. In the following description, components that are the same as those described above are given the same reference signs, and redundant descriptions are omitted.

Figure 8:
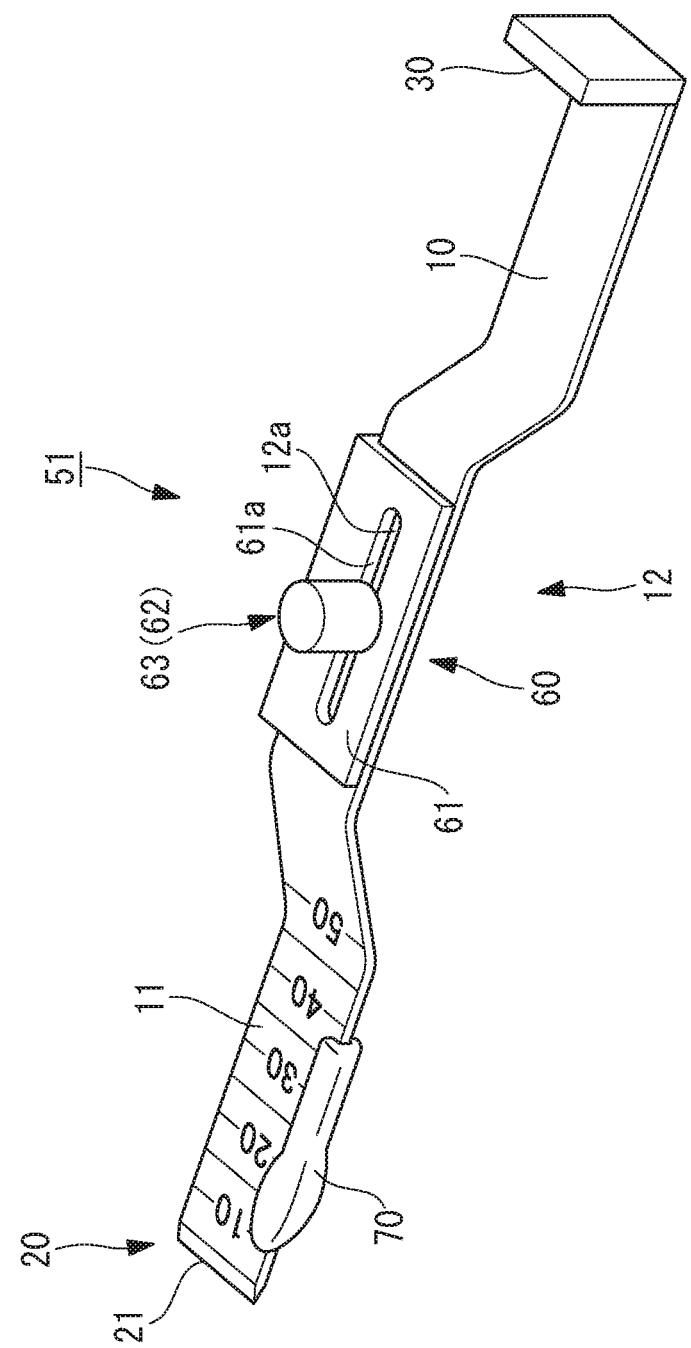
FIG. 8 is a perspective view illustrating an osteotomy surgical apparatus according to a third embodiment of the present invention.

FIG. 8 is a perspective view illustrating a surgical apparatus 51 according to this embodiment. In the main body 10 of the surgical apparatus 51, an intermediate section thereof in the longitudinal direction is displaced toward one side (i.e., the right side in this embodiment) in the width direction over a certain length (e.g., 40 to 80 mm), so that a crank segment 12 is formed. The shape and the maximum displacement amount (i.e., the maximum distance from other segments of the main body) of the crank segment 12 may be appropriately set, but preferably ranges from about 10 mm to 30 mm in view of functions to be described below.

The crank segment 12 according to this embodiment extends substantially parallel to the other segments of the main body 10. The crank segment 12 has a long hole 12a extending substantially parallel to the main body 10.

The crank segment 12 is provided with a stopper 60 for controlling the amount by which the surgical apparatus 51 is inserted into a biological organism. The stopper 60 has a plate 61 attached to the crank segment 12 and a locking screw 62 disposed to extend through the plate 61 and the crank segment 12.

The plate 61 has a long hole 61a with substantially the same shape and size as the long hole 12a, and is fixed to the crank segment 12 such that the long hole 12a and the long hole 61a are aligned with each other in plan view of the surgical apparatus 51.

The locking screw 62 has a screw section (not shown) having a thread groove and a knob section 63 provided at one end of the screw section. Because the diameter of the screw section is smaller than the width of the long holes 12a and 61a, the screw section can move freely within the long holes 12a and 61a. The knob section 63 has a columnar shape with a diameter larger than the width of the long holes 12a and 61a and thus cannot be inserted through the long holes 12a and 61a.

The locking screw 62 can be positioned at any position relative to the long holes 12a and 61a by inserting the screw section through the long holes 12a and 61a and tightly fastening a fastening screw (not shown) to the protruding end of the screw section.

Figure 9:
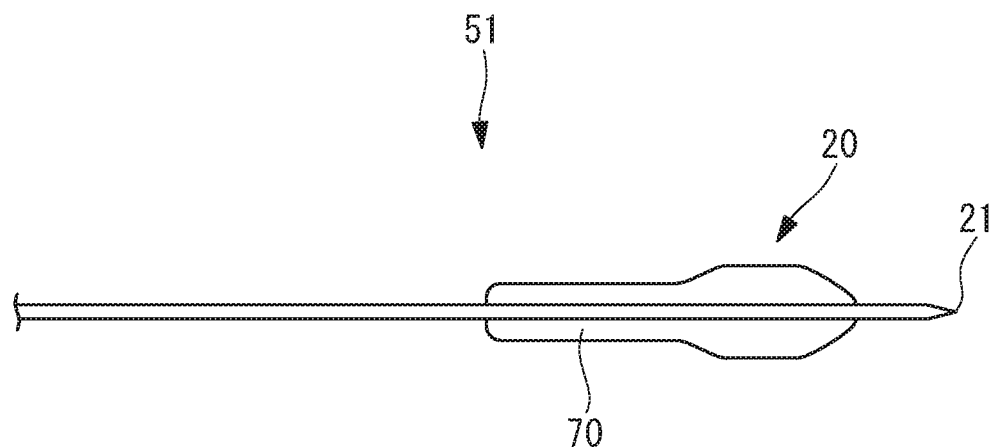
FIG. 9 is a partially enlarged view of the bone cutting blade of the surgical apparatus and the periphery thereof, as viewed from the right side.
Figure 10:
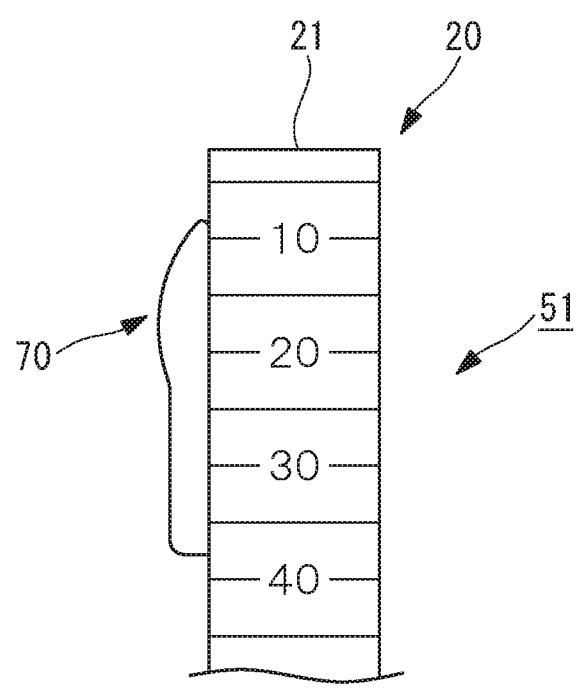
FIG. 10 is a partially enlarged view of the bone cutting blade and the periphery thereof, as viewed from above.

FIG. 9 is a partially enlarged view of the bone cutting blade 20 of the surgical apparatus 51 and the periphery thereof, as viewed from the right side. FIG. 10 is a partially enlarged view of the bone cutting blade 20 and the periphery thereof, as viewed from above. As shown in FIGS. 9 and 10, a guard 70 according to this embodiment substantially has a spoon-like shape such that the width and thickness at the distal end thereof are larger than the width and thickness at the base end thereof.

The operation when the surgical apparatus 51 is in use will now be described.

Figure 11:
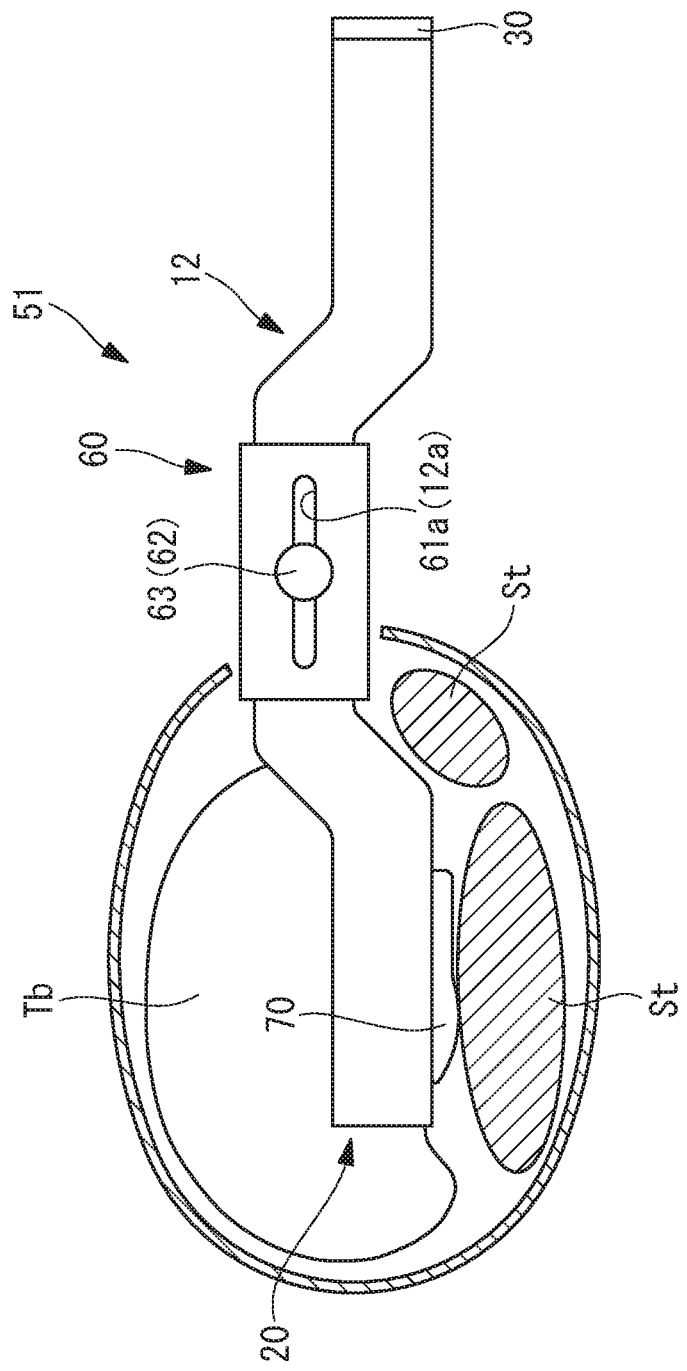
FIG. 11 schematically illustrates the surgical apparatus driven into a shin bone, as viewed from the head.

FIG. 11 schematically illustrates the surgical apparatus 51 driven into the shin bone Tb, as viewed from the head. When the surgical apparatus 51 is inserted into a biological organism and the depth by which the bone cutting blade 20 is inserted into the biological organism reaches a predetermined value, the knob section 63 of the stopper 60 comes into contact with the shin bone Tb or another tissue, thus making it impossible to drive the surgical apparatus 51 inward any further. Consequently, even when a surgeon accidentally strikes the striking section 30 with large force, the stopper 60 prevents the surgical apparatus 51 from being driven inward more than a predetermined amount. An upper value for the insertion depth of the bone cutting blade 20 regulated by the stopper 60 can be appropriately adjusted within the range of the length of the long holes 12a and 61a by moving the locking screw 62.

As shown in FIG. 11, soft tissue St exists not only at the dorsal side of the shin bone Tb but also at the inner side (i.e., the side closer toward the trunk of the body). The inner side has many soft tissues rich in collagen, such as ligaments. Collagen-rich soft tissues are highly resilient and repel back when pushed by the main body of a surgical apparatus. The surgical apparatus 51 according to this embodiment has the crank segment 12 in the intermediate section of the main body 10 in the longitudinal direction so that when the surgical apparatus 51 is driven into the shin bone Tb, the crank segment 12 is positioned more toward the front side (i.e., the ventral side) than the segment inserted in the shin bone Tb. As a result, the surgical apparatus 51 is less likely to come into contact with soft tissue located at the inner side of the shin bone, thereby favorably suppressing a situation where the orientation of the blade edge of the bone cutting blade is changed by a reaction force received from soft tissue.

Figure 12:
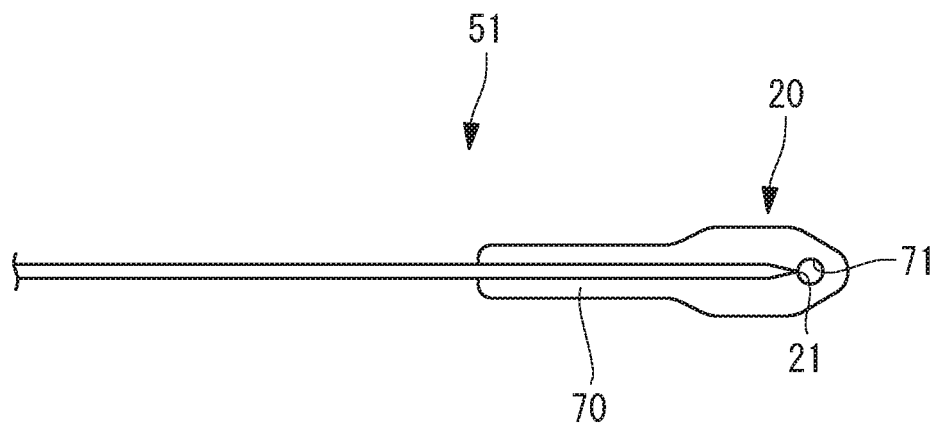
FIG. 12 is a partially enlarged view of a bone cutting blade according to a modification of the surgical apparatus and the periphery thereof, as viewed from the right side.

Similar to the second embodiment, in this embodiment, the guard 70 may be attached to the bone cutting blade 20 via the main body 10 in a slidable manner between the first position and the second position in the direction parallel to the longitudinal direction of the main body 10. In this case, as shown in FIG. 12, it is preferable that the distal end of the guard 70 be provided with a circular through-hole serving as a window (indicator) 71. The position of a part of the window 71 closest toward the base end and the position of the blade edge 21 of the bone cutting blade 20 are substantially aligned in the longitudinal direction of the surgical apparatus 51.

When the surgical apparatus 51 is inserted deep into tissue, it is difficult to properly ascertain the position of the blade edge 21 by viewing the operative field. Therefore, where necessary, the position of the blade edge is checked by using an X-ray image taken from the ventral side.

It is already described above that, in an HTO in the related art, an osteotomy is performed while separating soft tissue from a shin bone by using, for example, a metallic retractor. When checking the position of the blade edge by using an X-ray image in a procedure in the related art, since neither a surgical apparatus, such as a bone chisel, nor a retractor transmits an X ray, it is sometimes not possible to ascertain the position of the blade edge due to it being hidden by the retractor.

Figure 13:
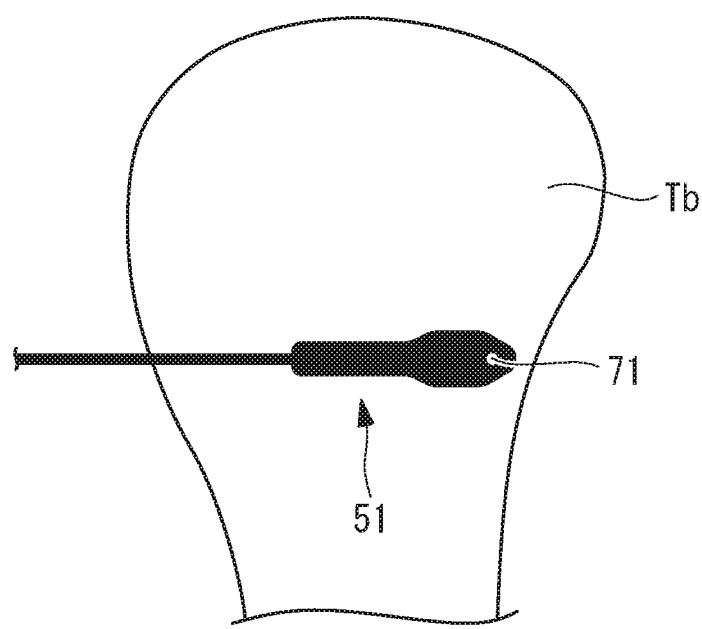
FIG. 13 is an image diagram illustrating an X-ray image taken in a state where the surgical apparatus according to the modification is driven into a shin bone.
Figure 14:
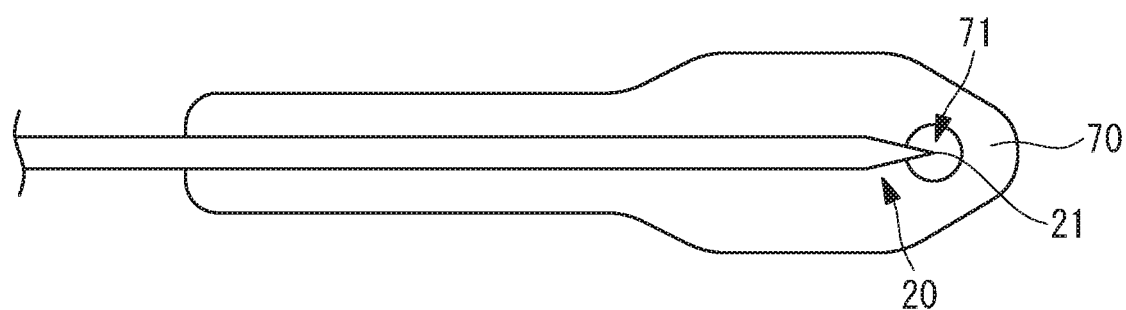
FIG. 14 illustrates a guard according to another modification of the surgical apparatus.

FIG. 13 is an image diagram illustrating an X-ray image taken in a state where the surgical apparatus 51 having the window 71 is driven into a shin bone. As shown in FIG. 13, the window 71 is clearly visible in the X-ray image so that the surgeon can readily ascertain the positional relationship between the position of the blade edge 21 and the shin bone Tb. As a result, the procedure can be performed more reliably.

The configuration of the indicator is not limited to the window 71 described above, and various modifications are possible. For example, according to a modification shown in FIG. 14, the guard 70 is attached to the bone cutting blade 20 such that the blade edge 21 is located within the region of the window 71, whereby the position of the blade edge 21 can be ascertained more reliably.

Figure 15:
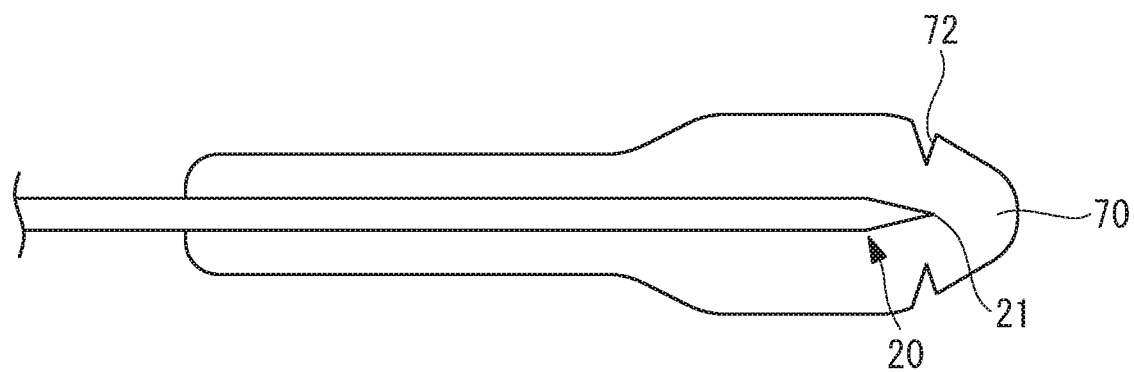
FIG. 15 illustrates a guard according to another modification of the surgical apparatus.

Furthermore, according to a modification shown in FIG. 15, a cutout 72 serving as the indicator may be provided at the position of the guard 70 that corresponds to the blade edge.

Moreover, the guard 70 may be composed of a material, such as resin, having higher X-ray transmissivity than the bone cutting blade 20. This prevents the main body 10 and the bone cutting blade 20 from being hidden by the guard 70 even if an indicator is not provided, whereby the position of the blade edge 21 can be properly ascertained. It should be noted that, even in this case, it is not forbidden to provide an indicator for making the position of the blade edge 21 more easily ascertainable.

It is preferable that the resin material used for forming the guard 70 be highly biocompatible and be sterilizable. Examples include fluorine-based resin, such as polyetheretherketone (PEEK), and polyphenylene sulfide (PPS).

The indicator may also be applied to the guard 40 according to the second embodiment, and the material with high X-ray transmissivity may also be applied to the guard 40 according to the first and second embodiments.

Figure 16:
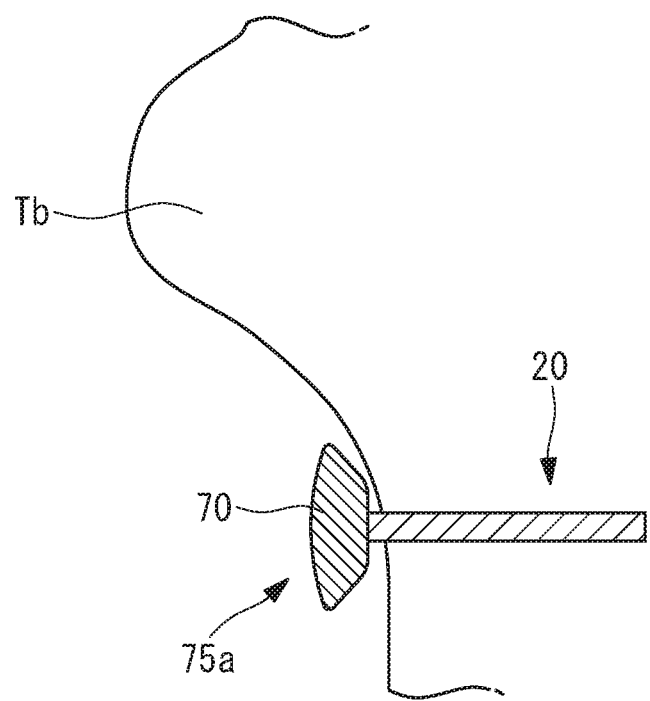
FIG. 16 illustrates the shape of a guard according to another modification of the surgical apparatus.

Furthermore, according to a modification shown in FIG. 16, a surface 75a located at one of the outer surfaces of the guard 70 in the thickness direction of the main body 10 may be inclined toward the bone cutting blade 20. Accordingly, when making an incision near the proximal end of the shin bone Tb, the guard can be readily disposed along the outer surface of the shin bone, thereby suppressing a state where a large reaction force acts on the main body when the guard comes into contact with the shin bone or a state where a large force is applied to the shin bone.

The configuration of the stopper is also not limited to the stopper 60 described above, and various known types of mechanisms may be appropriately employed.

Fourth Embodiment

Next, a fourth embodiment of the present invention will be described with reference to FIGS. 17 to 20. This embodiment is an example in which the structure of the surgical apparatus according to the present invention is applied to an electric bone saw.

Figure 17:
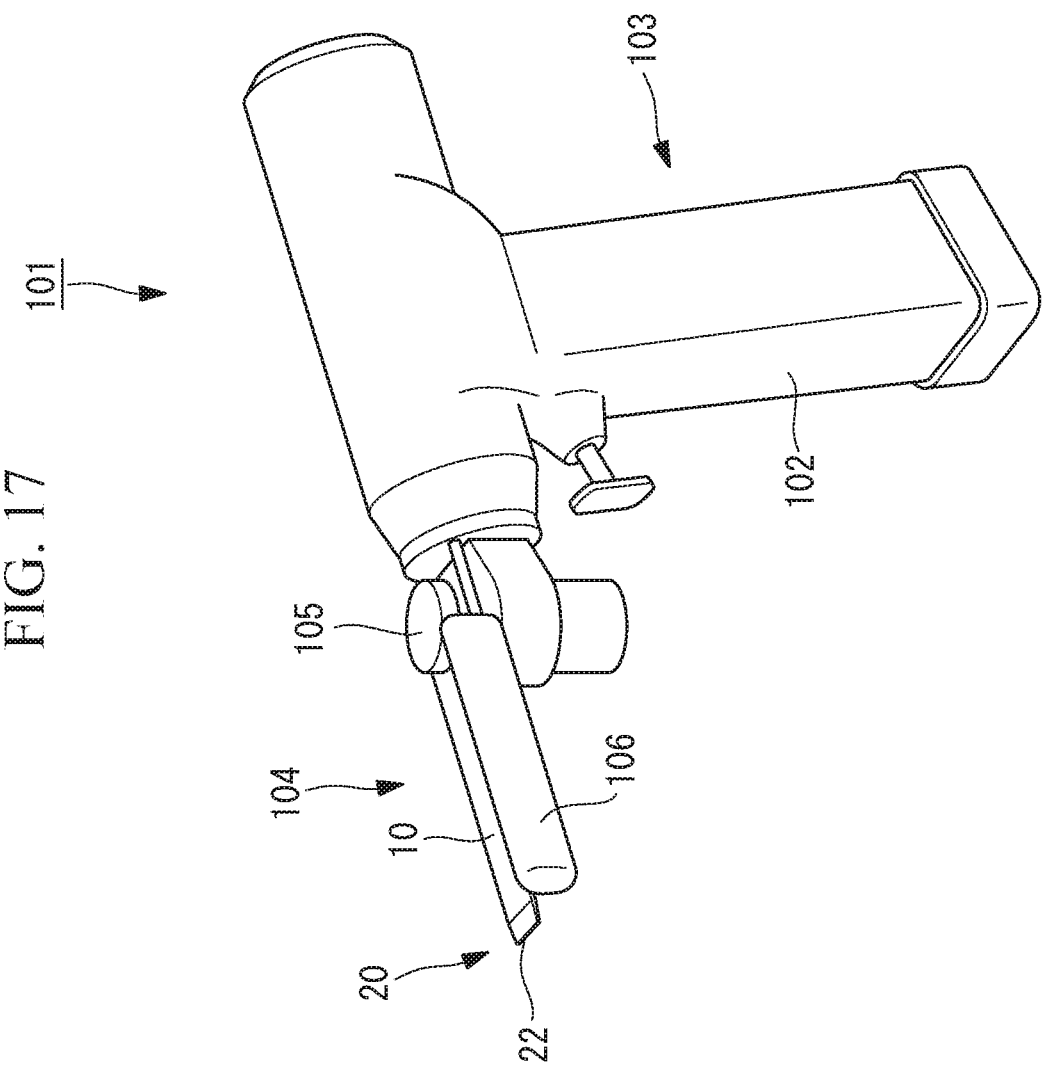
FIG. 17 is a perspective view illustrating an osteotomy surgical apparatus according to a fourth embodiment of the present invention.

FIG. 17 is a perspective view illustrating a surgical apparatus 101 according to this embodiment. The surgical apparatus 101 includes a main body 103 having a grip 102 held by a surgeon, and also includes a blade 104 attached to the main body 103.

The main body 103 is provided with a rotatable shaft 105. The rotatable shaft 105 receives electric power supplied from a power source contained in the main body 103 or connected to the main body 103 so as to alternately repeat forward and reverse rotations within a predetermined range (e.g., 10 degrees) about its own central axis.

The blade 104 has the main body 10 and the bone cutting blade 20 that are substantially similar to those in the first embodiment, and the base end of the blade 104 is fixed to the rotatable shaft 105 in a detachable manner. A blade edge 22 is serrated.

According to the above configuration, the surgical apparatus 101 functions as an electric bone saw.

A guard 106 has a base end fixed to the main body 103 and is attached to the main body 103 so as to extend substantially parallel to the blade 104 in a stationary state. The distal end of the guard 106 is disposed at a position retracted rearward relative to the blade edge 22.

Figure 18:
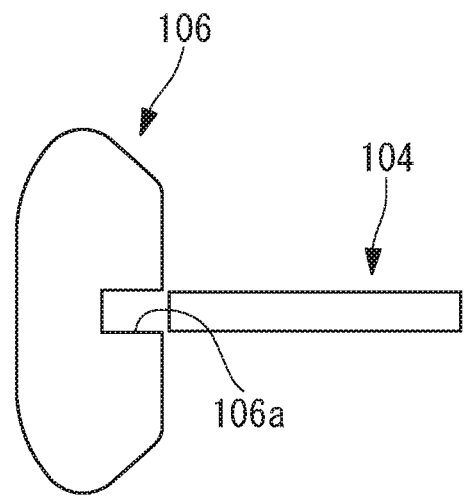
FIG. 18 illustrates a guard and a blade of the osteotomy surgical apparatus, as viewed from the base end.
Figure 19:
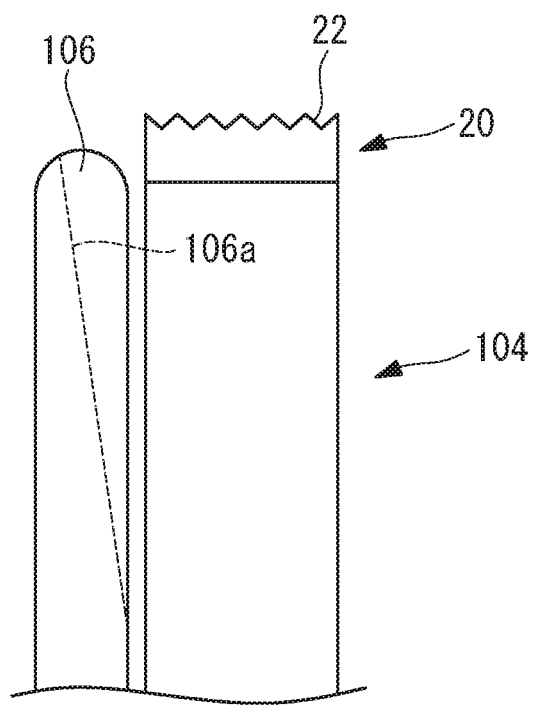
FIG. 19 illustrates the guard and the blade, as viewed from above.

FIG. 18 illustrates the guard 106 and the blade 104, as viewed from the base end. The guard 106 has a groove 106a at a position facing the blade 104 and having a width that allows the blade 104 to be inserted thereto. As shown in FIG. 19, the groove 106a is formed such that the depth thereof is the smallest at the base end of the guard 106 and gradually increases toward the distal end. Accordingly, even when the blade 104 rotates about the rotatable shaft 105 and moves maximally toward the guard 106, the blade 104 and the guard 106 do not interfere with each other.

Similar to the above embodiments, the surgical apparatus 101 according to this embodiment can be used to perform an osteotomy at the dorsal side of a shin bone to a desired position regardless of the shape of the bone, while minimizing effects on soft tissue existing around the bone.

Similar to the second embodiment, in this embodiment, the guard 106 may be biased toward the distal end by a biasing means such that the guard 106 is positionally aligned with the blade edge 22 in a side view of the bone cutting blade 20, and may be slidable rearward. In this case, the indicator described in the third embodiment may be provided in the guard.

Furthermore, the guard 106 may be composed of a material having higher X-ray transmissivity than the bone cutting blade 20.

Figure 20:
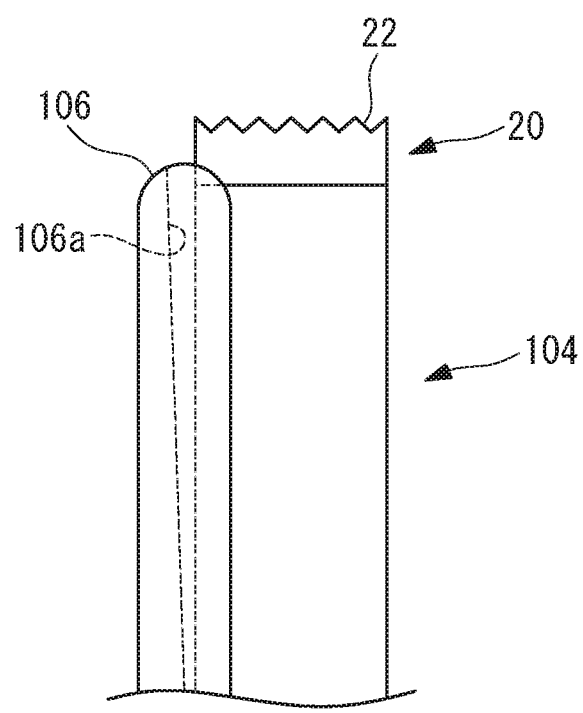
FIG. 20 illustrates a guard and a blade according to a modification of the osteotomy surgical apparatus, as viewed from above.

As an alternative to this embodiment in which the guard and the blade are separated from each other when the blade is in a stopped state, the blade 104 and the guard 106 may be disposed such that the blade 104 is partially positioned within the groove 106a when the blade 104 is in a stopped state, as shown in FIG. 20.

Furthermore, although not shown, the guard may be directly attached to the blade, similarly to the first to third embodiments. Accordingly, when the blade is driven, the guard is also driven together therewith, but if the vibration range of the blade is small enough, such a configuration can still withstand practical use.

Although the embodiments of the present invention have been described above, the technical scope of the present invention is not limited to the above-described embodiments. The combination of components in the embodiments and the modifications may be altered or the components may be modified or omitted so long as they do not depart from the scope of the invention.

For example, in the first to fourth embodiments, the guard may be disposed away from the bone cutting blade instead of being directly attached to the bone cutting blade. Even in this case, if the guard is disposed such that the guard overlaps the bone cutting blade in a side view of the bone cutting blade, effects on soft tissue can still be favorably minimized. In this case, the ends of the guard may be connected directly or via another component to, for example, the main body or the striking section.

Furthermore, although the guard may be disposed such that the distal end of the guard is positioned farther toward the base end than the distal end of the bone cutting blade, it is preferable that the guard be disposed so as to overlap the entire bone cutting blade, excluding the distal end thereof.

Moreover, the outer surface of the guard that does not face the bone cutting blade may be a curved surface so as to minimize excessive pressure applied to soft tissue.

In addition, the osteotomy surgical apparatus according to the present invention is not necessarily limited to use in an HTO. Specifically, the osteotomy surgical apparatus according to the present invention can be suitably used in an operative procedure other than an HTO if the operative procedure involves an osteotomy for a site surrounded by soft tissue.

As a result, the following aspect is read from the above described embodiment of the present invention.

A first aspect of the present invention provides an osteotomy surgical apparatus including: a bone cutting blade used for cutting bone tissue; and a guard disposed so as to overlap the bone cutting blade in a side view of the bone cutting blade, wherein a distal end of the guard is disposed at a position retracted rearward relative to a blade edge of the bone cutting blade.

According to this aspect, because the blade edge of the bone cutting blade protrudes more than the guard, the distal end of the guard is prevented from abutting on the bone before the blade edge does. Accordingly, the blade edge is made to reach a desired position of the bone regardless of the shape of the bone, so that an incision can be reliably made up to the desired position of the bone.

A second aspect of the present invention provides an osteotomy surgical apparatus including: a bone cutting blade used for cutting bone tissue; and a guard, wherein the guard is biased by a biasing means at least toward a position where the guard overlaps a blade edge of the bone cutting blade, and is slidable rearward in accordance with a force received from the bone tissue.

According to this aspect, when the distal end of the guard abuts on the bone before the blade edge does, the guard slides rearward against the biasing force of the biasing means, thereby preventing the guard from being stopped.

Accordingly, the blade edge is made to reach a desired position of the bone regardless of the shape of the bone, so that an incision can be reliably made up to the desired position of the bone. In this aspect, it is preferable that the guard is disposed at a position where the guard overlaps at least the blade edge of the bone cutting blade in a side view of the bone cutting blade.

In the first and second aspects, the bone cutting blade may be provided at a distal end of a plate-like main body, and the main body may have a crank segment in an intermediate section thereof in a longitudinal direction, the crank segment being displaced relative to another segment of the main body.

In the first and second aspects, the guard may have a curved outer surface.

In the first and second aspects, the guard may have an indicator in correspondence with a position of the blade edge.

In the first and second aspects, the guard may be composed of a material having higher X-ray transmissivity than the bone cutting blade.

REFERENCE SIGNS LIST 1, 51, 101 osteotomy surgical apparatus
10 main body
12 crank segment
20 bone cutting blade
21, 22 blade edge
40, 70, 106 guard
60 stopper
71 window (indicator)
72 cutout (indicator)

The invention claimed is:

1. An osteotomy surgical apparatus comprising:
a plate-like main body extending in a longitudinal direction from a first end to a second end,
a bone cutting blade configured to cut bone tissue, the bone cutting blade having a proximal end connected to the first end of the main body, the bone cutting blade tapering from a first thickness at the proximal end to a blade edge at a distal end of the bone cutting blade;
a striking section that is provided at a second end of the main body; and
a guard that is fixed relative to the bone cutting blade such that the guard covers a side surface of the bone cutting blade in a side view of the bone cutting blade, a distal end surface of the guard being positioned at the side surface between the proximal end and the distal end of the bone cutting blade.

2. The osteotomy surgical apparatus according to claim 1, wherein the main body has a crank segment positioned between the first end and the second end, the crank segment being displaced in a direction offset from the longitudinal direction relative to another segment of the main body.

3. The osteotomy surgical apparatus according to claim 1, wherein the guard has a curved outer surface.

4. The osteotomy surgical apparatus according to claim 1, wherein the guard has an indicator in correspondence with a position of the blade edge.

5. The osteotomy surgical apparatus according to claim 1, wherein the guard is composed of a material having higher X-ray transmissivity than the bone cutting blade.

* * * * *